(12) United States Patent
Prestidge et al.

(10) Patent No.: US 8,303,992 B2
(45) Date of Patent: Nov. 6, 2012

(54) DRIED FORMULATIONS OF NANOPARTICLE-COATED CAPSULES

(75) Inventors: Clive Allan Prestidge, Semaphore South (AU); Spomenka Simovic, Adelaide (AU)

(73) Assignee: University of South Australia, Adelaide, South Australia (AU)

( * ) Notice: Subject to any disclaimer, the term of this patent is extended or adjusted under 35 U.S.C. 154(b) by 0 days.

(21) Appl. No.: 12/902,769

(22) Filed: Oct. 12, 2010

(65) Prior Publication Data

US 2011/0027454 A1 Feb. 3, 2011

Related U.S. Application Data

(63) Continuation of application No. 11/916,570, filed as application No. PCT/AU2006/000771 on Jun. 7, 2006, now abandoned.

(30) Foreign Application Priority Data

Jun. 7, 2005 (AU) .............................. 2005902937

(51) Int. Cl.
*A61K 9/51* (2006.01)
(52) U.S. Cl. .................... 424/490; 977/773; 977/797
(58) Field of Classification Search ........................ None
See application file for complete search history.

(56) References Cited

U.S. PATENT DOCUMENTS

| | | | |
|---|---|---|---|
| 3,850,655 A | 11/1974 | Adams | |
| 5,185,155 A | 2/1993 | Behan et al. | |
| 5,500,223 A | 3/1996 | Behan et al. | |
| 5,670,139 A | 9/1997 | Allard et al. | |
| 5,876,755 A | 3/1999 | Perring et al. | |
| 6,391,321 B1 * | 5/2002 | Gers-Barlag et al. | 424/401 |
| 6,585,983 B1 | 7/2003 | Gers-Barlag et al. | |
| 2003/0175317 A1 * | 9/2003 | Barthel et al. | 424/401 |
| 2004/0001891 A1 | 1/2004 | Smith et al. | |
| 2004/0202682 A1 | 10/2004 | Emrick et al. | |
| 2005/0006800 A1 | 1/2005 | Mountziaaris et al. | |

(Continued)

FOREIGN PATENT DOCUMENTS

EP 0478326 A1 4/1992

(Continued)

OTHER PUBLICATIONS

KL Christensen, GP Pedersen, HG Kristensen. "Physical Stability of Redispersible Dry Emulsions Containing Amorphous Sucrose." European Journal of Pharmaceutics and Biopharmaceutics. vol. 53, 2002, pp. 147-153.*

(Continued)

*Primary Examiner* — Frederick Krass
*Assistant Examiner* — Isaac Shomer
(74) *Attorney, Agent, or Firm* — Rothwell, Figg, Ernst & Manbeck PC

(57) ABSTRACT

A method of producing a dried formulation for an active substance such as a drug compound is described. The method involves dispersing a discontinuous phase (e.g. an oil-based or lipidic medium) comprising the active substance into a continuous phase (e.g. water) so as to form a two-phase liquid system comprising droplets of said discontinuous phase, allowing nanoparticles to congregate at the phase interface at the surface of the droplets such that at least one layer of nanoparticles coat the droplets and thereby provide sufficient structural integrity to the droplets to enable the subsequent removal of the continuous phase, and thereafter removing the continuous phase from the nanoparticle-coated droplets to produce a dried formulation.

15 Claims, 7 Drawing Sheets

U.S. PATENT DOCUMENTS

Figure 1:
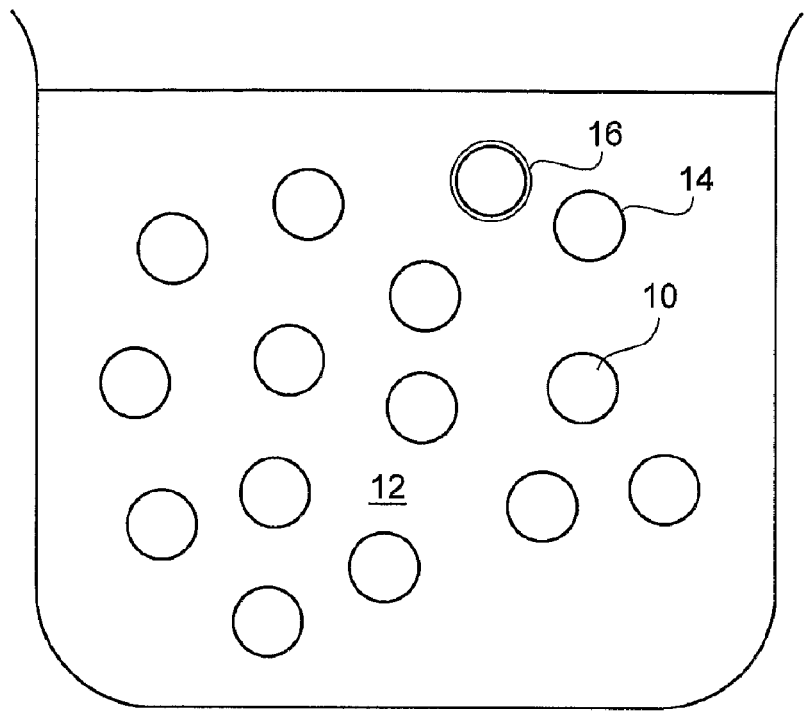

| | | |
|---|---|---|
| 2006/0083781 A1 | 4/2006 | Shastri et al. |
| 2009/0181076 A1 | 7/2009 | Prestidge et al. |
| 2009/0263486 A1 | 10/2009 | Prestidge et al. |

FOREIGN PATENT DOCUMENTS

| | | |
|---|---|---|
| WO | 0247665 A2 | 6/2002 |
| WO | 03082232 A1 | 10/2003 |
| WO | 2006133518 A1 | 12/2006 |
| WO | 2007128066 A1 | 11/2007 |
| WO | 2008128292 A1 | 10/2008 |

OTHER PUBLICATIONS

CA Prestidge, T Barnes, S Simovic. "Polymer and particle adsorption at the PDMS droplet-water interface." Advances in Colloid and Interface Science, vol. 108-109, 2004, pp. 105-118.*

JD Weete, S Betageri, GL Griffith. "Improvement of Lecithin as an Emulsifier for Water-in-Oil Emulsions by Thermalization." JAOCS, vol. 71, No. 7, Jul. 1994, pp. 731-737.*

Hsu, Ming F., "Charged Colloidal Particles in Nonpolar Solvents and Self-assembled Colloidal Model Systems," A thesis presented to the Department of Physics, Harvard Univaersity, Cambridge, Massachusetts, Sep. 2004, 111 pages.

Noble, Paul F., et al., "Fabrication of 'Hairy' Colloidosomes with Shells of Polymeric Mlcrorods," J. Am. Chem. Soc. 126: 8092-8093 (2004).

Hwang, Yi-Jeong, et al., "Controlled release of retinol from silica particles prepared in O/W/O emulsion: The effects of surfactants and polymers," Journal of Controlled Release, 106: 339-349 (2005).

Dinsmore, A.D., "Colloidosomes: Selectively Permeable Capsules Composed of Colloidal Particles," Science, 298: 1006-1009 (Nov. 1, 2002).

Zhang, Liangfang, et al., "How to Stabilize Phospholipid Liposomes (Using Nanoparticles)," Nano Letters, 6:4, 694-698 (2006). First published on web Feb. 22, 2006.

Simovic, Spomenka, et al., "Hydrophilic Silica Nanoparticles at the PDMS Droplet—Water Interface," Langmuir, 19: 3785-3792 (2003).

Simovic, Spomenka, et al., "Adsorption of Hydrophobic Silica Nanoparticles at the PDMS Droplet-Water Interface," Langmuir, 19:20, 8364-8370 (2003).

Simovic, Spomenka, et al., "Nanoparticles of Varying Hydrophobicity at the Emulsion Droplet-Water Interface: Adsorption and Coalescence Stability," Langmuir, 20:8357-8365 (2004).

Prestidge, Clive A., "Polymer and particle adsorption at the PDMS droplet-water interface," Advances in Colloid and Interface Science, 108-109: 105-118 (2004).

Wang, Dayang, "The water/oil interface: the emerging horizon for self-assembly of nanoparticles," Soft Matter, 1:6, 412-416 (2005). First published on web Oct. 26, 2005.

Daniels, Rolf, scf-online.com, Issue 25, Daniels: Galenic principles of modern skin care products, Skin Care Forum, Issue 25, Apr. 2001 (online) <URL: http://www.scf-online.com/english/25_e/galenic_25_e.htm>. This site was first captured by the internet archive Waybackmachine on May 22, 2001.

CA Prestidge, T Barnes, S Simovic. "Polymer and Particle Adsorption at the PDMS Droplet-Water Interface." Advances in Colloid and Interface Science, 108-109, 2004, pp. 105-118.

KL Christensen, GP Pedersen, HG Kristensen. "Preparation of Redispersible Dry Emulsions by Spray Drying." International Journal of Pharmaceutics, vol. 212, 2001, pp. 187-194.

Derwent On-line Abstract Accession No. 2004-611106.59 (2004).

Prestidge, C.A., et al., Poster titled "Nanoparticle coated droplets: a platform delivery system for lipophlic drugs," Pharmaceutical Sciences World Congress, Amsterdam, The Netherlands, Apr. 22-25, 2007.

Tan, A., et al., Poster titled Nanoparticle Encapsulated Droplets: A Novel Delivery System for Lipophilic Drugs, 34th Annual Meeting & Exposition of the Controlled Release Society, Long Bech Convention Center, Long Beach, California, USA, Jul. 7-11, 2007.

Bos, J.D., et al., "The 500 Dalton rule for the skin penetration of chemicl compounds and drugs," Exp. Dermatol., 9:165-169 (2000).

Jennings, V., et al., "Vitamin A loaded solid lipid nonoparticles for topical use: occulusive properties and drug targeting to the upper skin," European Journal of Pharmaceutics and Biopharmaceutics, 49(3): 211-218 (2000).

Rowe, Raymond C., et al. (Ed.), Handbook of Pharmaceutical Excipients, Fifth Edition, Pharmaceutical Press, 6 pages (2005).

* cited by examiner

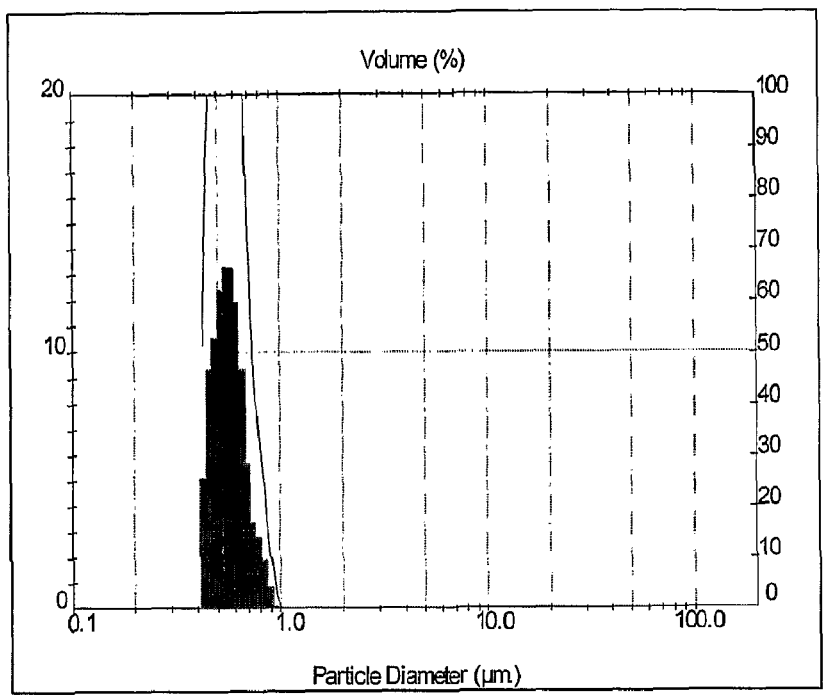

Fig 7a

| Result: Analysis Table | | | |
|---|---|---|---|
| ID: | Run No: 1 | | Measured: 11/10/04 3:41PM |
| File: (Result Not Saved) | | | Analysed: 11/10/04 3:41PM |
| Path: D:\ | | | Source: Analysed |
| Range: 100 mm | Beam: 14.30 mm | Sampler: MSX3 | Obs': 99.8 % |
| Presentation: 2OHD | | Analysis: Polydisperse | Residual: 1.062 % |
| Modifications: None | | | |
| Conc. = 0.0144 %Vol | Density = 2.600 g/cm^3 | | S.S.A.= 4.5229 m^2/g |
| Distribution: Volume | D[4, 3] = 0.55 um | | D[3, 2] = 0.51 um |
| D(v, 0.1) = 0.46 um | D(v, 0.5) = 0.56 um | | D(v, 0.9) = 0.71 um |
| Span = 4.538E-01 | Uniformity = 1.905E-01 | | |

| Size (um) | Volume In % | Size (um) | Volume In % | Size (um) | Volume In % | Size (um) | Volume In % |
|---|---|---|---|---|---|---|---|
| 0.20 | | 1.84 | | 8.48 | | 39.08 | |
| 0.48 | 17.96 | 2.23 | 0.00 | 10.27 | 0.00 | 47.30 | 0.00 |
| 0.59 | 42.48 | 2.70 | 0.00 | 12.43 | 0.00 | 57.25 | 0.00 |
| 0.71 | 29.54 | 3.27 | 0.00 | 15.05 | 0.00 | 69.30 | 0.00 |
| 0.86 | 8.90 | 3.95 | 0.00 | 18.21 | 0.00 | 83.87 | 0.00 |
| 1.04 | 1.08 | 4.79 | 0.00 | 22.04 | 0.00 | 101.52 | 0.00 |
| 1.26 | 0.04 | 5.79 | 0.00 | 26.68 | 0.00 | 122.87 | 0.00 |
| 1.52 | 0.00 | 7.01 | 0.00 | 32.29 | 0.00 | 148.72 | 0.00 |
| 1.84 | 0.00 | 8.48 | 0.00 | 39.08 | 0.00 | 180.00 | 0.00 |

Fig 7b

DRIED FORMULATIONS OF NANOPARTICLE-COATED CAPSULES

This application is a continuation of U.S. Ser. No. 11/916,570, filed Dec. 5, 2007 which is a 371 filing of PCT/AU2006/000771, filed Jun. 7, 2006 which claims priority from Australian Patent Application No. 2005902937, filed Jun. 7, 2005. These prior applications are incorporated herein by reference.

FIELD OF THE INVENTION

The present invention relates to the encapsulation by nanoparticles of a liquid droplet or a lipid vesicle to form a stable capsule.

BACKGROUND OF THE INVENTION

The development of new forms of active substances such as drug compounds and pesticides, as well as a desire to increase the efficacy of existing substances, has created a need to develop new and effective ways of delivering substances to their appropriate targets. It is likely that many potentially useful active substances have not been commercialised because of inadequate formulation. In many cases, the inability to formulate the active substance into a deliverable form could simply be due to solubility problems.

Although useful as vehicles for the delivery of active substances, most emulsions and liposomes are limited by the fact they are thermodynamically unstable and, generally, over time, will coalesce and may eventually separate into two distinct liquid phases (emulsions) or will degrade and release the fluid-filled core into the surrounding media (liposomes). This instability is exacerbated in veterinary and pharmacological applications since the vehicles are used under circumstances (e.g. increased salt (electrolyte) or variations in pH) which put a severe strain on the vehicle structure. The degradation of vehicles containing active substances is undesirable since considerable time and effort is spent in formulating the delivery system. In the veterinary, pharmaceutical and nutriceutical industries in particular, if vehicle stability is compromised, the bioavailability of the active substance may be affected.

Particle stabilised emulsions are known, however, the stability of the resulting capsules remains poor over a period of time. This means that it is difficult to transport the capsules over long distances and it is difficult to store the capsules for a delayed time of use. As the capsules degrade, the active substance (e.g. a drug compound or a pesticide) within the capsules can leach out, or may be released without control. Leaching or uncontrolled release of active substances can pose a serious problem in the delivery of certain drugs in the body, since one intent of the encapsulation process is to shield healthy cells from the drug's toxicity and prevent the drug from concentrating in vulnerable tissues (e.g. the kidneys and liver).

Existing preparations of particle stabilised vehicles (capsules) are usually dispersed in a liquid in order that the capsules can be delivered to the body as a liquid suspension. These liquid formulations usually have a low active substance content to liquid ratio and, in addition, during storage or transport, there is a risk of microbial growth in the liquid which can cause serious infections or spoilage.

A further problem is coalescence of the capsules to form capsules with an increased diameter. Larger capsules are less stable over time, and larger capsules cannot be delivered to some areas where the diameter of the capsule will not be permitted (e.g. capillaries in the body). Further to this, active substance release profiles are correlated with interfacial surface area. It is important, therefore, that capsule size remain constant in order that the release profile of the active substance is maintained.

Accordingly, it is an object of the present invention to provide a capsule for the delivery and/or dry storage of an active substance which has a relatively long shelf-life and is therefore easy to store or transport and may have a reduced risk of microbial growth during storage.

SUMMARY OF THE INVENTION

A method of producing a dried formulation for an active substance, said method comprising the steps of:
(i) dispersing a discontinuous phase comprising an active substance into a continuous phase so as to form a two-phase liquid system comprising droplets of said discontinuous phase, each of said droplets having, at its surface, a phase interface;
(ii) allowing nanoparticles provided to said two-phase liquid system to congregate at the phase interface to coat said surface of the droplets in at least one layer of said nanoparticles, wherein said at least one layer of nanoparticles provides sufficient structural integrity to the droplets to enable the subsequent removal of the continuous phase; and
(iii) removing the continuous phase from the nanoparticle-coated droplets to produce a dried formulation.

The discontinuous phase may be dispersed in the continuous phase to form a two-phase liquid system (e.g. an emulsion) by any of the methods well known to persons skilled in the art (e.g. by homogenisation).

Preferably, the discontinuous phase is an oil-based or lipidic medium (e.g. a phospholipid preparation), and the continuous phase is aqueous.

However, alternatively, the discontinuous phase is aqueous and the continuous phase is an oil-based or lipidic medium.

Also alternatively, the discontinuous phase is aqueous and each droplet is surrounded by a single or multiple lipid bilayer (i.e. thereby forming a liposome), and the continuous phase is also aqueous.

Either or both of the discontinuous and continuous phases may comprise an emulsifier to stabilise the emulsion prior to the congregation of the nanoparticles. Suitable emulsifiers include lecithin, oleylamine, sodium deoxycholate, 1,2-distearyl-sn-glycero-3-phosphatidyl ethanolamine-N, stearylamine and 1,2-dioleoyl-3-trimethylammonium-propane. Preferably, the emulsifier is oleylamine which confers a positive charge to the droplets.

The emulsifier will typically be provided in an amount in the range of 0.0001 to 10 wt % of the emulsion, more preferably, in the range of 0.01 to 1 wt % of the emulsion.

The active substance may be selected from nutriceutical substances, cosmetic substances (including sunscreens), pesticide compounds, agrochemicals and foodstuffs. However, preferably, the active substance is selected from drug compounds. The active substance may be a biological agent such as a peptide, protein or nucleic acid (e.g. deoxyribonucleic acid (DNA)). Such biological agents are particularly suitable for formulation within capsules comprising liposomes.

The nanoparticles may have hydrophilic or hydrophobic surfaces. However, when the discontinuous phase is an oil-based or lipidic medium, preferably the nanoparticles will have hydrophilic surfaces. In one preferred embodiment, the droplets will be coated with a single layer, or multiple layers, of hydrophilic nanoparticles. However, in another preferred embodiment, the droplets will be coated with at least two layers of nanoparticles, the inner layer of nanoparticles having hydrophobic surfaces while the outer layer of nanoparticles have hydrophilic surfaces.

The nanoparticles may be positively or negatively charged.

Preferably, said nanoparticles have an average diameter of 5-2000 nm, more preferably 20-80 nm, and most preferably about 50 nm. Also, preferably, the size of the nanoparticles will be such that the ratio of nanoparticle size to the size of the nanoparticle-coated droplets (i.e. capsules) is in the range of 1:4 to 1:20 and, more preferably, is about 1:10.

Preferably, the nanoparticles are composed of silica, however nanoparticles composed of other substances (e.g. titania and latex) are also suitable.

Congregation of the nanoparticles (e.g. by self-assembly and/or adsorption) at the phase interface results in the coating of the surface of the droplets in at least one layer of nanoparticles such that sufficient structural integrity is provided to the droplets so that they may withstand removal of the continuous phase to produce a dried formulation. By "structural integrity", it is to be understood that the capsules substantially retain the active substance (i.e. the capsules do not exhibit substantial leaching of the active substance) and do not substantially coalesce with one another to form larger capsules over time. To achieve such structural integrity may require providing the nanoparticles to the two-phase liquid system within a particular concentration range.

Preferably, the congregation of the nanoparticles at the phase interface occurs in the presence of an amount of electrolyte suitable to enhance the congregation of the nanoparticles at the phase interface. The amount of the electrolyte will typically be at least $0.5 \times 10^{-4}$ M, preferably, at least $1 \times 10^{-3}$ M. However, preferably, the concentration of electrolyte will be no more than $1 \times 10^{-1}$ M.

Preferably, the electrolyte is NaCl.

The removal of the continuous phase is a drying step which may be performed using a rotary evaporator. Alternatively, the removal of the continuous phase may be performed by freeze drying, spray drying or fluidised bed procedures.

Following step (ii) but prior to the drying step, additional nanoparticles may be added to the two-phase liquid system, if desired.

The capsules of the dried formulation may be readily re-dispersed into a liquid to re-form a two-phase liquid system. In particular, the re-dispersed capsules may form a capsule-based emulsion (which might be a capsule-based liposome emulsion) which is substantially identical or similar in composition to that from which the dried formulation was prepared after storage at room temperature for 24 hours, and more preferably, after storage at room temperature for 2 months. "Substantially identical or similar" in this context is intended to mean that the average diameter size of the capsules is the same or varies from the original capsules by no more than a factor of about 4 times (i.e. the average diameter size of the re-dispersed capsules is no more than 4 times greater in size or 4 times less in size than the original capsules). Further, preferably, few (if any) of the re-dispersed capsules have a diameter size greater than 10 µm; for example, preferably less than 5% of the re-dispersed capsules, by volume, have a diameter size of greater than 10 µm). The re-dispersed capsules are stable and typically show no substantial degradation after 24 hours storage at room temperature (i.e. after 24 hours, the average diameter size of the re-dispersed capsules remains at no more than 4 times greater in size or 4 times less in size than the original capsules, and preferably less than 5% of the re-dispersed capsules, by volume, have a diameter size of greater than 10 µm).

In a variation of the present invention, prior to the removal of the continuous phase, the capsules may be provided with a polymer layer around the periphery to modify the interfacial properties of the capsule.

In a further variation, the discontinuous phase may, optionally, be cross-linked or otherwise comprise a gelling material so as to form a matrix. While re-dispersed capsules from dried formulations produced in accordance with the present invention are permeable (i.e. the nanoparticle coating will be porous), and thereby typically show controlled release of the active substance at rates dependent upon the degree of permeability (e.g. a capsule with a lower degree of permeability (i.e. a "semi-permeable" capsule), will show sustained release of the active substance), the inclusion of a cross-linked or gelled matrix within the discontinuous phase can be used to provide further control to the release of the active substance from the capsules, particularly sustained release.

In a still further variation of the present invention, the nanoparticles provided to the two-phase liquid system congregate at the phase interface while the continuous phase is being removed (i.e. during the drying step).

Thus, in a second aspect, the present invention provides a method of producing a dried formulation for an active substance, said method comprising the steps of:

(i) dispersing a discontinuous phase comprising an active substance into a continuous phase so as to form a two-phase liquid system comprising droplets of said discontinuous phase, each of said droplets having, at its surface, a phase interface; and (ii) removing the continuous phase to produce a dried formulation, during which nanoparticles provided to said two-phase liquid system congregate at the phase interface to coat said surface of the droplets in at least one layer of said nanoparticles, wherein said at least one layer of nanoparticles provides sufficient structural integrity to the droplets to withstand the removal of the continuous phase.

The method of the second aspect is particularly suitable wherein the droplets are negatively charged, and the nanoparticles to be used are negatively charged, hydrophilic nanoparticles.

In a third aspect, the present invention provides a dried formulation for an active substance, said formulation comprising droplets formed by dispersing a discontinuous phase comprising an active substance into a continuous phase so as to form a two-phase liquid system, wherein each droplet is coated in at least one layer of said nanoparticles and the continuous phase has been removed.

The formulation comprises droplets formed by dispersing a discontinuous phase into a continuous phase to form a two-phase liquid system. As with the methods of the first and second aspects of the present invention, preferably the discontinuous phase is an oil-based or lipidic medium and the continuous phase is aqueous. Either or both of the discontinuous and continuous phases may comprise an emulsifier (e.g. lecithin) to stabilise the emulsion prior to coating with at least one layer of nanoparticles.

The active substance may be selected from those mentioned above.

Preferably, said nanoparticles have an average diameter of 5-2000 nm, more preferably 20-80 nm, and most preferably about 50 nm. Also, preferably, the size of the nanoparticles will be such that the ratio of nanoparticle size to capsule size is in the range of 1:4 to 1:20 and, more preferably, is about 1:10.

Preferably, the nanoparticles are composed of silica, however nanoparticles composed of other substances (e.g. titania and latex) are also suitable.

The capsules of the dried formulation may be readily re-dispersed into a liquid to re-form a two-phase liquid system. In particular, the re-dispersed capsules may form a capsule-based emulsion which is substantially identical or similar in composition to that from which the dried formulation was prepared.

In variations of the formulation of the present invention, the capsules may be provided with a polymer layer around the periphery to modify the interfacial properties of the capsule. Also, the discontinuous phase may, optionally, be cross-linked or otherwise comprise a gelling material so as to form a matrix, which may enable controlled release of an active substance (i.e. sustained release) from the capsules.

Figure 2:
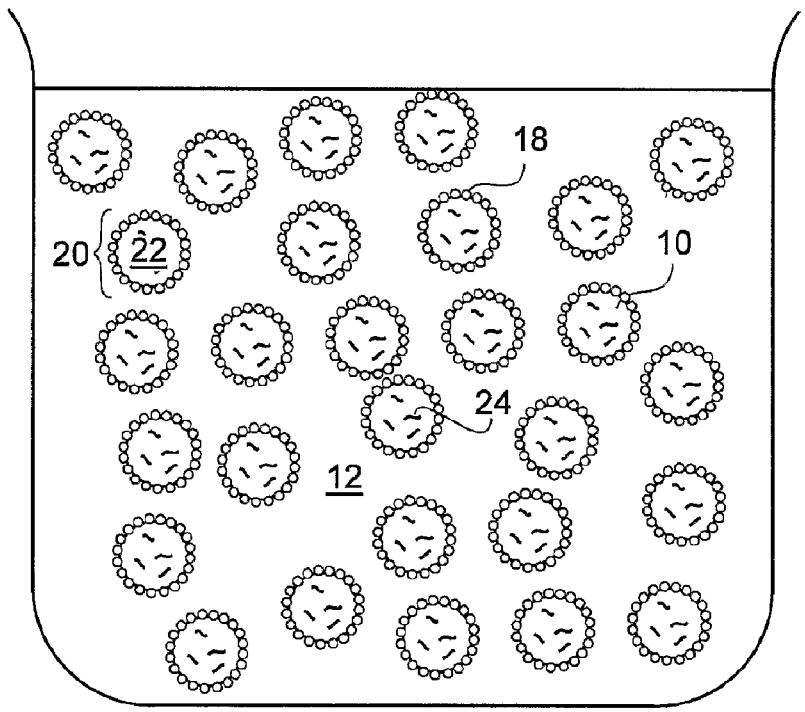

The present invention provides a method for producing dried formulations of nanoparticle-coated capsules comprising a drug compound. An advantage of such formulations is that the dried capsules (e.g. in the form of a dry powder), have a long shelf life and do not exhibit substantial leaching of the drug compound over times that drug formulations are commonly stored (e.g. 1 to 9 months). In addition, the capsules have a low propensity to coalescence. The dried capsules can be readily re-dispersed into a liquid to re-form a stable emulsion, thereby providing a useful drug formulation for the pharmaceutical industry. The capsules can be readily stored and/or transported dry.

In addition, the nanoparticle coating on the droplets of the capsules can protect labile active substances (i.e. chemically unstable substances) from degradation caused by acidity (i.e. low pH), oxidation and crystallisation, etc. The nanoparticle coating is also resistant to water (i.e. the nanoparticle coat does not substantially expand or degrade in the presence of water).

The ability to protect the active substances from the degradative effects of acidity, makes the dried formulation of the present invention particularly useful in the oral administration of labile drug compounds (i.e. where it is desirable that the drug compound be protected from the high acidity of the stomach before reaching the small intestine where the drug compound may be adsorbed into the bloodstream).

In a further aspect, the present invention provides a formulation for an active substance, said formulation comprising droplets formed by dispersing a discontinuous phase comprising an active substance into a continuous phase so as to form a two-phase liquid system, wherein each droplet is coated in at least one layer of said nanoparticles.

The formulation of the further aspect can be dried or, otherwise, can be used in its liquid form.

In one preferred embodiment of the formulation of the further aspect, the capsules are provided with a polymer layer around the periphery to modify the interfacial properties of the capsule. In this way, the capsules may be made to be "lipoadhesive", particularly if the polymer layer has adhesive properties with lipid-like surfaces. One significant aspect of this is that the capsules can be then be engineered to adhere to particular sites in vivo (e.g. mucoadhesive polymer layers facilitate adhesion to mucous membranes), thereby ensuring long contact times and effective transport of the active substance. This can be particularly useful for the delivery of poorly soluble drug compounds to various parts of the gastrointestinal tract (i.e. to improve bioavailability). It may also be used to facilitate delivery of an active substance to the mouth.

The combination of polymers and nanoparticles at the capsule surface can lead to further controlled release properties.

The invention will be generally discussed hereinafter in relation to drug delivery from emulsions but it is not so restricted and as mentioned above, nanoparticles may congregate at the phase interface of other suitable vehicles (e.g. liposomes and solid particles).

Throughout this specification and the claims that follow unless the context requires otherwise, the words "comprise" and "include" and variations such as "comprising" and "including" will be understood to imply the inclusion of a stated integer or group of integers but not the exclusion of any other integer or group of integers.

The reference to any prior art in this specification is not, and should not be taken as, an acknowledgment or any form of suggestion that such prior art forms part of the common general knowledge.

Specific embodiments of the invention will now be described in some further detail with reference to and as illustrated in the accompanying figures. These embodiments are illustrative, and not meant to be restrictive of the scope of the invention. Suggestions and descriptions of other embodiments may be included within the scope of the invention but they may not be illustrated in the accompanying figures or alternatively features of the invention may be shown in the figures but not described in the specification.

BRIEF DESCRIPTION OF THE DRAWINGS

An illustrative embodiment of the present invention is discussed hereinafter with reference to the accompanying drawings wherein:

FIG. 1 is a cross-sectional schematic of an emulsion known in the art;

FIG. 2 is a cross-sectional schematic of a nanoparticle-stabilised emulsion according to the present invention;

FIG. 3 is a graph to show adsorption isotherms of hydrophilic silica nanoparticles assembling at the oil water interface;

FIG. 4 is a graph to show adsorption isotherms of hydrophobic silica nanoparticles assembling at the oil water interface;

FIG. 5 is a flow chart showing the steps involved in obtaining the dry capsules of the present invention;

FIG. 6 is a schematic of the processes involved in obtaining the capsules of the present invention as well as showing the re-dispersion of the capsules;

FIG. 7*a* shows the emulsion droplet size range;

FIG. 7*b* is the tabular form of FIG. 7*a*, showing the emulsion droplet size range;

FIG. 8 shows the average diameter of the silica nanoparticles in nanometers; and FIG. 9 shows the long-term physical stability of negatively charged emulsions in the presence of increasing concentrations of hydrophilic silica nanoparticles.

DESCRIPTION OF PREFERRED EMBODIMENT

FIG. 1 is a cross-sectional schematic of a two-phase liquid system referred to as an emulsion having a discontinuous oil phase in the form of droplets 10 dispersed in a continuous aqueous phase 12, thereby defining a phase interface 14. After a period of time, adjacent oil droplets 10 will coalesce (the beginning of phase separation) to form larger oil droplets. If an emulsion is not stabilised by an emulsifier localised in the thin film 16, then coalescence of the emulsion will occur within minutes. Eventually the oil phase 10 and aqueous phase 12 will have completely separated into the two component phases (oil and water).

FIG. 2 shows the system of FIG. 1 where droplets 10 have been stabilised by nanoparticles 18 at the interface 14. Two otherwise immiscible liquids (10 and 12) have thereby formed a stabilised emulsion (nb. FIG. 2 is a schematic and nanoparticles 18 are not drawn to scale with respect to droplets 10).

In the preferred embodiment, as described above, the discontinuous phase is an oil-based or lipidic medium and the continuous phase is aqueous. However, the discontinuous phase may be an aqueous phase dispersed in an oil-based or lipidic medium. Further, the discontinuous phase may be aqueous and each droplet surrounded by a single or multiple lipid bilayer (i.e. thereby forming a liposome), and the continuous phase is also aqueous.

In order to improve biocompatibility of the emulsion, the oil phase can be a fatty-food simulant such as a triglyceride (e.g. Miglycol 812™) Alternatively, the oil phase can be a silicone such as polydimethlysiloxane (PDMS), or any other oily medium which will form an emulsion with an aqueous phase.

Nanoparticles 18 are dispersed in a liquid by sonication and provided to the emulsion in order to coat each droplet 10 in at least one layer of nanoparticles. In a preferred embodiment, the liquid dispersion comprises 1% by weight (1 wt %) of nanoparticles in an aqueous medium (i.e. 1 g of nanoparticles per 100 ml). However, other weight % dispersions can be usefully employed. Upon addition, the nanoparticles congregate at the phase interface 14 (e.g. by self-assembly). Alternatively, rather then being added to the preformed emulsion, nanoparticles 18 can be first dispersed in either phase (i.e. the oil or aqueous phase) or both phases (i.e. the oil and the water phase) and, as an emulsion is formed, nanoparticles 18 will congregate at the phase interface 14. Nanoparticles 18 form at least a partial coating over the surface of droplets 10 (phase interface 14). The resulting nanoparticle-coated droplet is referred to as a capsule 20.

Preferably, the ratio of nanoparticle size to capsule size is between 1:4 and 1:20. The nanoparticles 18 which stabilise the emulsion may have an average diameter in the range 5 nm-2000 nm and may be made from any suitable material (e.g. titania or latex). Preferably, the nanoparticles are silica nanoparticles having an average diameter of between 20-80 nm. In the preferred embodiment, the nanoparticles have an average diameter of approximately 50 nm and the capsule diameter size ranges between 200-850 nm with an average capsule size of approximately 500 nm. The approximate ratio of nanoparticle to capsule size is therefore, preferably about 1:10.

In a preferred embodiment, the nanoparticles are Aerosil® silica nanoparticles (Degussa AG, Dusseldorf, Germany). The surfaces of nanoparticles 18 may be chemically or physically modified to hydrophobise the nanoparticles 18.

Capsule 20 has a liquid core 22 (the discontinuous phase) which may comprise or contain active substance 24. Preferably, the liquid core 22 is a hydrophobic or lipidic medium and contains a lipophilic active substance 24 therein. It is an option, however, that the liquid core 22 is aqueous and has a hydrophilic active substance 24 dissolved therein. In FIG. 2, the cross-sectional depiction shows active substance 24. The active substance may be any substance which is required to be protected and/or delivered by capsule 20. The active substance may be selected from nutriceutical substances, cosmetic substances (including sunscreens), pesticide compounds, agrochemicals and foodstuffs. In the preferred embodiment, the active substance 24 is a drug compound.

The active substance 24 may be wholly or partially soluble or dispersible within liquid core 22. Also, the oil phase may, optionally, be cross-linked or otherwise comprise a gelling material so as to form a matrix which can enable controlled release of an active substance (i.e. sustained release) from the capsules.

It is an option that the outer surface of the capsules 20 be coated with a layer that improves the interfacial properties of the capsules. For example, in drug delivery, capsules 20 may be further coated with a polymer layer around the periphery of capsule 20 to increase the bioadhesivity of the capsule to cells within the body. Such a layer may comprise a polymer selected from methylcellulose, hydroxypropylcellulose, ethylcellulose, polyethyleneglycols, chitosan, guar gum, alginates, eudragit and pemulen, etc. Other coatings around the capsule 20 which improve or modify the interfacial properties of the capsule may be used. An example of the preparation of a coated capsule is given in Example 5.

Drying the Capsules

A delivery system which is dry and can be transported, stored and/or administered as a powder is an advantage in many industries, such as the pharmaceutical industry, since dry powder formulations usually have a higher active substance content compared with an aqueous formulation. This means that less volume of the delivery system is required for administration of an effective amount of active substance. The increase in active substance content in dry formulations is mainly due to the elimination of unnecessary liquids.

Figure 5:
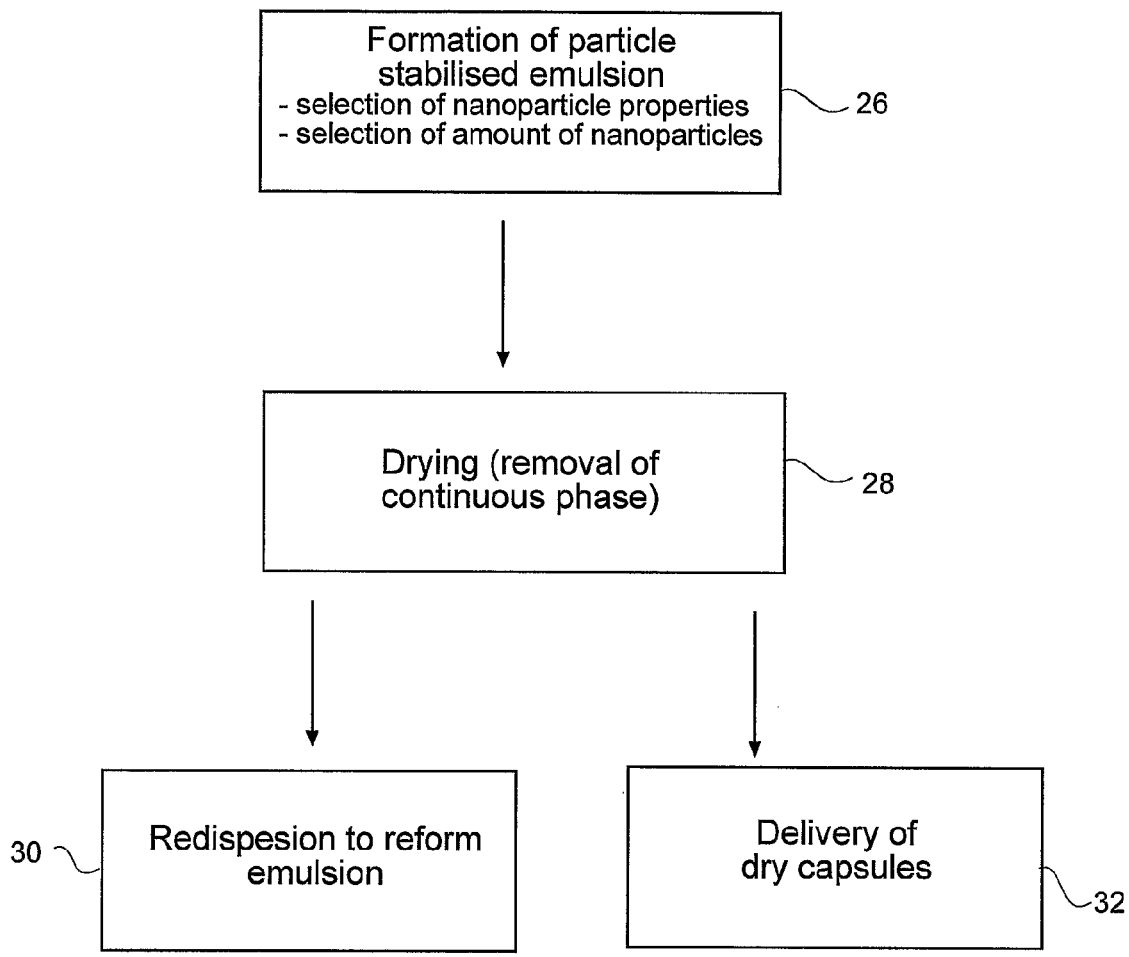

FIG. 5 is a flow chart outlining the processes involved in obtaining the dried formulation. In step 26, the amount (i.e. volume of nanoparticle 1 wt % dispersion) of nanoparticles and, optionally, the properties of nanoparticles 18, provided to the emulsion, are selected or otherwise controlled so that capsules 20 can withstand the removal of the continuous phase during a subsequent drying step (discussed further below). The nanoparticles should provide sufficient structural integrity to the coated droplets (capsules) to enable the subsequent removal of the continuous phase to produce the dry formulation. A capsule having "structural integrity" substantially retains the active substance within its core and does not exhibit substantial leaching of the active substance and also does not substantially coalesce with other capsules to form larger capsules over time. To achieve such structural integrity may require providing the nanoparticles to the two-phase liquid system within a particular concentration range as described below.

The emulsion can be dried by any suitable method, for example freeze drying, spray drying or fluidised bed techniques. In step 28, the emulsion is dried by spray-drying and the resulting dried capsules are collected in a suitable vessel.

Figure 6:
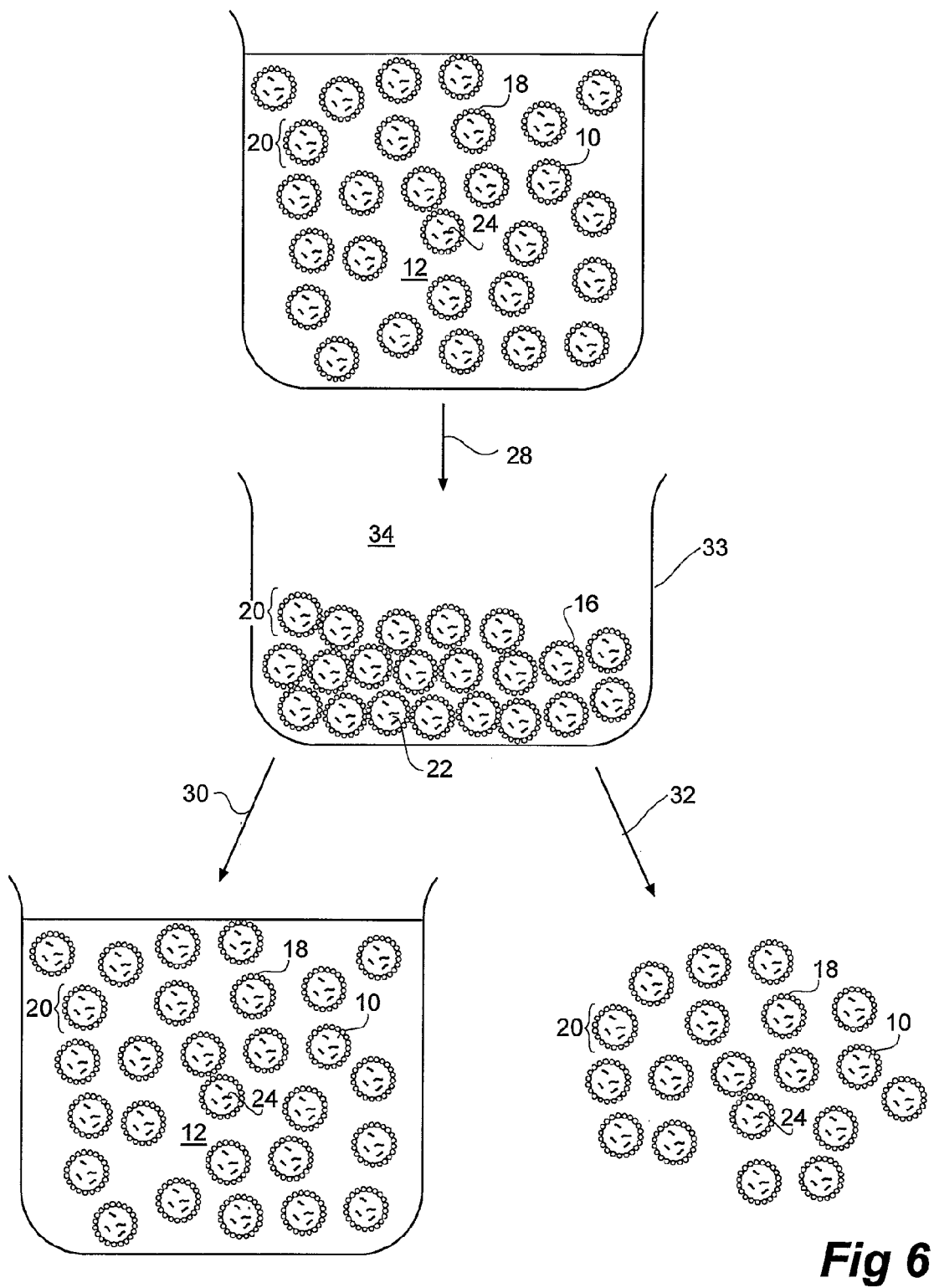

FIG. 6 depicts the dried capsules 20 in vessel 33. Dried capsules 20 have nanoparticles 18 congregated at their surface 14. Once dried, it is an option that dried capsules 20 are delivered in dry form (step 32). Dry formulations have increased active substance loading, thereby reducing the amount of formulation that is required. A further advantage is that the risk of microbial growth, which can cause serious infections or spoilage, is reduced in dry formulations compared with liquid formulation.

Not all capsules formed in the wet phase are able to be dried (i.e. some capsules lack the abovementioned structural integrity). Table 1 below shows the results of a number of experiments in which the capsules collapsed during the drying step.

Table 1 shows that of the 27 different tested variations (using hydrophilic silica nanoparticles with an average diameter of about 50 nm, and an oil-based discontinuous phase stabilised with lecithin (negatively charged oil droplets) or oleylamine (positively charged droplets) within an aqueous continuous phase), 19 combinations formed capsules which maintained their structural integrity during removal of the continuous phase. In the first six rows of the table, a dry powder of capsules could not be obtained due to loss of structural integrity and subsequent degradation of capsules. The experiments shown in rows G-τ show the oil to nanoparticle mass ratios which formed dry capsules.

It can be seen that an oil to nanoparticle mass ratio of at least 1:0.05 was required in order to be able to produce dried capsules with positively charged droplets, and that an oil to nanoparticle mass ratio of at least 1:0.2 was required in order to be able to produce dried capsules with negatively charged droplets.

TABLE 1

Emulsion and hydrophilic silica nanoparticle amounts to produce dry capsules.
The oil droplets were stabilised with lecithin or oleylamine.

| Row | Label | Volume of emulsion (10 wt % oil) | Volume of particles (1 wt %) | Mass of oil | Mass of particles | [NaCl] in overall mixture volume ($1 \times 10^{-x}$ M) | Overall mixture volume | Ratio of Oil (wt):particles (wt) |
|---|---|---|---|---|---|---|---|---|
| A | Dried capsules not obtained | 10 ml | 10 ml | 1 g | 0.1 g | $10^{-4}$ | 20 ml | 1:0.1 |
| B | Dried capsules not obtained | 10 ml | 10 ml | 1 g | 0.1 g | $10^{-2}$ | 20 ml | 1:0.1 |
| C | Dried capsules not obtained | 10 ml | 5 ml | 1 g | 0.05 g | $10^{-4}$ | 20 ml | 1:0.05 |
| D | Dried capsules not obtained | 10 ml | 5 ml | 1 g | 0.05 g | $10^{-2}$ | 20 ml | 1:0.05 |
| E | Dried capsules not obtained | 10 ml | 1 ml | 1 g | 0.01 g | $10^{-4}$ | 20 ml | 1:0.01 |
| F | Dried capsules not obtained | 10 ml | 1 ml | 1 g | 0.01 g | $10^{-2}$ | 20 ml | 1:0.01 |
| G | Dried capsules obtained | 1 ml | 10 ml | 0.1 g | 0.1 g | $10^{-4}$ | 20 ml | 1:1 |
| H | Dried capsules obtained | 1 ml | 10 ml | 0.1 g | 0.1 g | $10^{-2}$ | 20 ml | 1:1 |
| I | Dried capsules obtained | 1 ml | 10 ml | 0.1 g | 0.1 g | $10^{-1}$ | 20 ml | 1:1 |
| J | Dried capsules obtained | 1 ml | 10 ml | 0.1 g | 0.1 g | $10^{-4}$ | 11 ml | 1:1 |
| K | Dried capsules obtained | 1 ml | 5 ml | 0.1 g | 0.05 g | $10^{-4}$ | 20 ml | 1:0.5 |
| L | Dried capsules obtained | 1 ml | 5 ml | 0.1 g | 0.05 g | $10^{-2}$ | 20 ml | 1:0.5 |
| M | Dried capsules obtained | 1 ml | 5 ml | 0.1 g | 0.05 g | $10^{-1}$ | 20 ml | 1:0.5 |
| N | Dried capsules obtained | 1 ml | 5 ml | 0.1 g | 0.05 g | $10^{-4}$ | 6 ml | 1:0.5 |
| O | Dried capsules obtained | 1 ml | 5 ml | 0.1 g | 0.05 g | $10^{-2}$ | 6 ml | 1:0.5 |
| P | Dried capsules obtained | 1 ml | 5 ml | 0.1 g | 0.05 g | $10^{-4}$ | 10 ml | 1:0.5 |
| Q | Dried capsules obtained | 1 ml | 5 ml | 0.1 g | 0.05 g | $10^{-2}$ | 10 ml | 1:0.5 |
| R | Dried capsules obtained | 1 ml | 5 ml | 0.1 g | 0.05 g | $10^{-1}$ | 10 ml | 1:0.5 |
| S | Dried capsules obtained | 5 ml | 5 ml | 0.5 g | 0.05 g | $10^{-4}$ | 100 ml | 1:0.1 |

TABLE 1-continued

Emulsion and hydrophilic silica nanoparticle amounts to produce dry capsules.
The oil droplets were stabilised with lecithin or oleylamine.

| Row | Label | Volume of emulsion (10 wt % oil) | Volume of particles (1 wt %) | Mass of oil | Mass of particles | [NaCl] in overall mixture volume ($1 \times 10^{-x}$ M) | Overall mixture volume | Ratio of Oil (wt):particles (wt) |
|---|---|---|---|---|---|---|---|---|
| T | Dried capsules obtained | 5 ml | 15 ml | 0.5 g | 0.15 g | $10^{-4}$ | 100 ml | 1:0.3 |
| U | Dried capsules obtained | 5 ml | 25 ml | 0.5 g | 0.25 g | $10^{-4}$ | 100 ml | 1:0.5 |
| V | Dried capsules obtained | 5 ml | 50 ml | 0.5 g | 0.5 g | $10^{-4}$ | 100 ml | 1:1 |
| W | Dried capsules obtained | 5 ml | 95 ml | 0.5 g | 0.95 g | $10^{-4}$ | 100 ml | 1:2 |
| X | Dried Capsules obtained | 25 ml | 25 ml | 2.5 g | 0.25 g | $10^{-4}$ | 100 ml | 1:0.1 |
| Y | Dried capsules obtained | 25 ml | 50 ml | 2.5 g | 0.5 g | $10^{-4}$ | 100 ml | 1:0.2 |
| Z | Dried capsules obtained | 25 ml | 95 ml | 2.5 g | 0.95 g | $10^{-4}$ | 100 ml | 1:0.4 |
| α | Dried capsules obtained | 50 ml | 50 ml | 5 g | 0.5 g | $10^{-4}$ | 100 ml | 1:0.1 |
| β | Dried capsules obtained | 15 ml | 7.5 ml | 1.5 g | 0.075 g | $10^{-4}$ | 100 ml | 1:0.05 |
| Ψ | Dried capsules obtained | 15 ml | 15 ml | 1.5 g | 0.15 g | $10^{-4}$ | 100 ml | 1:0.1 |
| δ | Dried capsules obtained | 15 ml | 30 ml | 1.5 g | 0.3 g | $10^{-4}$ | 100 ml | 1:0.2 |
| ε | Dried capsules obtained | 25 ml | 12.5 ml | 2.5 g | 0.125 g | $10^{-4}$ | 100 ml | 1:0.05 |
| φ | Dried capsules obtained | 25 ml | 25 ml | 2.5 g | 0.25 g | $10^{-4}$ | 100 ml | 1:0.1 |
| γ | Dried capsules obtained | 25 ml | 47.5 ml | 2.5 g | 0.475 g | $10^{-4}$ | 100 ml | 1:0.2 |
| η | Dried capsules obtained | 50 ml | 25 ml | 5 g | 0.25 g | $10^{-4}$ | 100 ml | 1:0.05 |
| ι | Dried capsules obtained | 50 ml | 50 ml | 5 g | 0.5 g | $10^{-4}$ | 100 ml | 1:0.1 |

The capsules of experiments A to R, T to W, Y, Z, δ and γ were prepared from emulsions stabilised with lecithin (i.e. negatively charged droplets), while the capsules of experiments S, α to ψ, ε, φ, η and τ were prepared from emulsions stabilised with oleylamine (i.e. positively charged droplets). The capsules of experiments A to R were dried using rotary evaporation, while the capsules of experiments S to τ were dried using spray-drying.

Properties of Driable Capsules (1) Wettability of Nanoparticles

Nanoparticles 18 (e.g. silica nanoparticles) can be modified to be hydrophobic. In a preferred embodiment, the surfaces of nanoparticles 18 are modified with organosilanes (e.g. dimethylchlorosilane). The coalescence behaviour of capsule 20 is dependent upon the hydrophobicity or hydrophilicity of nanoparticles 18, as well as the coverage of nanoparticles 18 at the emulsion droplet interface 14. At full or partial coverage of hydrophilic nanoparticles 18, capsules 20 still display some degree of enlargement behaviour (i.e. the diameter of the capsules increase during coalescence). In contrast, emulsion droplets coated by more than one layer of hydrophobic nanoparticles 18 (under conditions of coagulation in the presence of high salt concentrations (e.g. $1 \times 10^{-1}$ M)), form stable flocculated networks rather than enlarged capsules. Experiments have revealed that in the wet phase, it is preferable that nanoparticles 18 have a hydrophobic surface which reduces the occurrence of capsule 20 coalescence.

However, while hydrophobic nanoparticles form a stable wet phase capsule with good protection of the active substance, further experiments have indicated that hydrophilic nanoparticles better stabilise capsules during a drying phase. That is, the results of these experiments have indicated that if the nanoparticles have a hydrophobic surface, then the capsules may be unstable during the drying step. This may be due to migration of the hydrophobic nanoparticles into the oil of the emulsion droplet, resulting in instability of the capsules. It is an option therefore, that droplets are first coated with a hydrophobic layer of nanoparticles to create a stable wet phase. The resulting capsules can then be further coated by a hydrophilic layer of nanoparticles to stabilise the capsule during a drying phase. The further coat of hydrophilic nanoparticles can be applied by adding the nanoparticles to the continuous phase and allowing them to congregate onto the surface of the capsule while the wet phase is "standing" and/or during the drying phase.

(2) Effect of Salt Concentration on Nanoparticle Congregation

Figure 3:
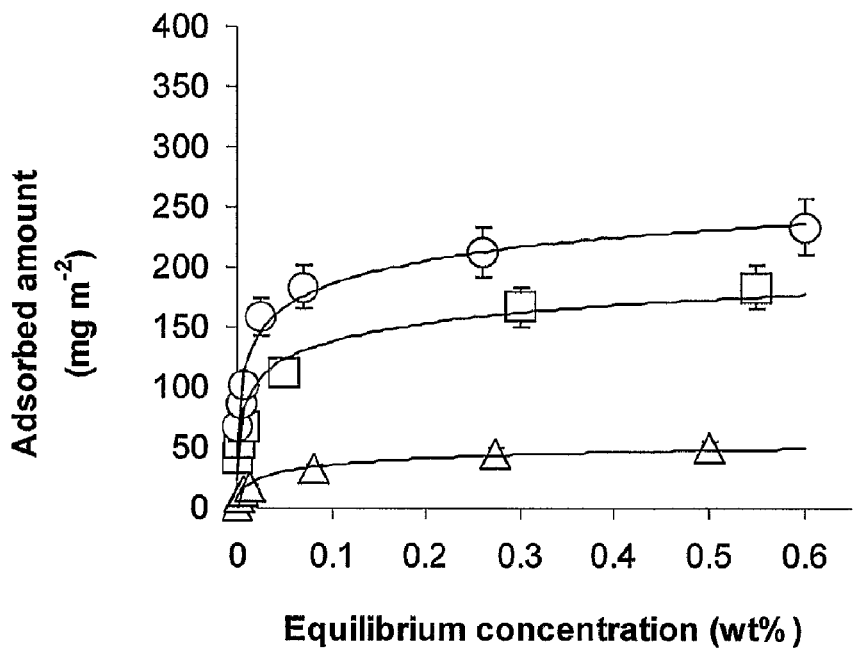
Figure 4:
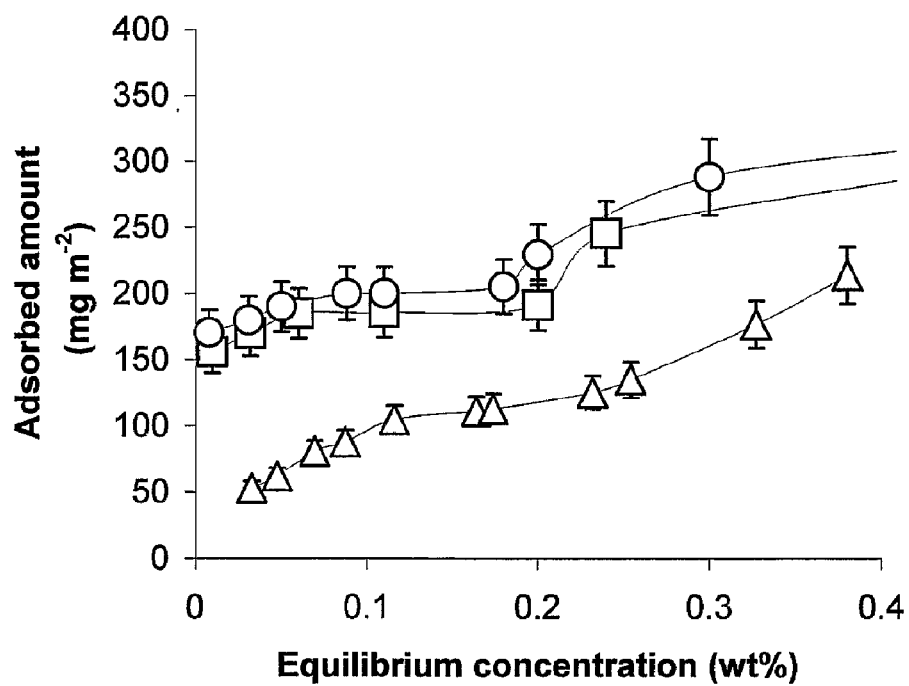

Typical isotherms for hydrophilic silica nanoparticles adsorbing at a model oil water interface 14 are shown in FIG. 3. It is clear that salt (electrolyte) addition dramatically increases nanoparticle adsorption. Preferably, the nanoparticles congregate at the phase interface in the presence of an amount of electrolyte suitable to enhance the congregation of the nanoparticles at the phase interface. The amount of the electrolyte will typically be less than $1\times10^{-1}$ M (preferably, at least $1\times10^{-3}$ M and more preferably, at least $0.5\times10^{-4}$ M). In the preferred embodiment, NaCl is used, however it will be understood by persons skilled in the art that any electrolyte may be used.

While not wishing to be bound by theory, it is considered that the free energy of nanoparticle adsorption increases significantly with salt addition due to a reduction in the range of nanoparticle-droplet and nanoparticle-nanoparticle lateral electrostatic repulsion. In high salt concentrations (e.g. $1\times10^{-2}$ and $1\times10^{-1}$ M NaCl), adsorption amounts for hydrophilic nanoparticles 18 correspond to approximately 75% and just over 100% of an equivalent hexagonally close-packed monolayer of hard spheres respectively. The fractional surface coverage is an approximation calculated from the ratio of adsorbed amount of nanoparticles 18 and the theoretical value for a hexagonally close packed monolayer (i.e. 200 $mg \cdot m^{-2}$ for 50 nm diameter nanoparticles).

(3) Effect of Charged Oil Droplets on Nanoparticle Congregation

It is an option that, prior to the addition of nanoparticles 18, a negatively charged phospholipid monolayer, such as lecithin or a positively charged oleylamine is used as a stabiliser to stabilise the oil droplets of the emulsion (emulsifier 14 is shown in FIG. 1). Both lecithin and oleylamine are fat emulsifiers which help to prevent droplets 10 from coalescing before nanoparticles 18 congregate. Other stabilisers similar to oleylamine, which are particularly useful in the present invention, include 1,2-distearyl-sn-glycero-3-phosphatidyl ethanolamine-N, stearylamine and 1,2-dioleoyl-3-trimethylammonium-propane.

Experiments have shown that negatively charged phospholipid stabilised triglyceride droplets do not strongly interact with hydrophilic silica nanoparticles. This is evidenced by adsorption studies, freeze fracture SEM and is supported by EDAX surface elemental analysis. Positively charged oleylamine stabilised triglyceride droplets on the other hand, strongly interact with hydrophilic silica nanoparticles as evidence by adsorption studies, charge reversal and freeze-fracture SEM.

(4) Phase from which Nanoparticles Congregate

As stated above, the nanoparticles can be first dispersed in either phase (oil or water) and, as an emulsion is formed, the nanoparticles will congregate at the phase interface.

Initial studies have shown that very few negatively charged nanoparticles from the aqueous phase (less than 5%) congregate at the droplet surface of negatively charged droplets (e.g. droplets stabilised with lecithin), although greater levels of nanoparticle congregation has been observed with droplets of silicone (i.e. PDMS). Positively charged droplets however, are coated by nanoparticles dispersed within the aqueous phase.

(5) Oil:Nanoparticle Mass Ratio

The oil (g) to nanoparticle (g) ratio plays an important role in preparing capsules which can withstand the drying step (i.e. driable capsules). That is, an oil to nanoparticle mass ratio of at least 1:0.02 is considered to be necessary in order to produce dried capsules. However, preferably, an oil to nanoparticle mass ratio of at least 1:0.05 and, more preferably, at least 1:0.2, is used.

Properties of Redispersible Capsules

The capsules are prepared so as to remain stable and do not substantially coalesce to form capsules with an increased diameter. The present invention therefore has the advantage of maintaining the release profile of the active substance contained within the capsule as well as maintaining the small size of the capsules. The small size of the capsules both increases surface area and allows the capsules to be delivered to target areas which require a small capsule size (e.g. blood capillaries). Capsules 20 may therefore have a longer shelf life than prior capsule formulations and can be stored and/or transported for later use.

Preferably, the dried capsules 20 can be re-dispersed (shown by step 30) in a liquid (preferably water) to re-form a stabilised emulsified product. Not all dried capsules are satisfactorily re-dispersible and again, the properties selected during capsule formation are important. Dried capsules in accordance with the present invention, however, can be made to re-disperse in a liquid to form an emulsion which is substantially identical or similar in composition to that from which the dried formulation was prepared. This means that the average capsule diameter size is the same or varies from the original capsule by no more than a factor of about 4 times and, preferably, shows few (i.e. less than 5% by volume), if any, capsules with a diameter size of greater than 10 µm.

The re-constitutive properties following the re-dispersion of capsules of Table 1 in phosphate buffer are shown in Table 2 below. The reconstitution mark rates how similar the reconstituted emulsion compared with the emulsion from which the capsules were dried.

The re-constitutive properties following re-dispersion of capsules of Table 1 in acidic medium after 2 months of storage at room temperature are shown in Table 3 below.

TABLE 2

Average capsule size and reconstitution rating following redispersion of capsules (in phosphate buffer (pH = 7.2)) listed in Table 1. 0.01 g of powder was dissolved in 4 g of phosphate buffer $10^{-4}$M after 24 hours from drying (size measured using Malvern Mastersizer)

| Row (from Table 1) | Oil:particle ratio | Average drop size before drying (μm) | Average re-dispersed drop size (μm) | D (v, 0.9) (μm) | Vol % above 10 μm | Reconstitution mark |
|---|---|---|---|---|---|---|
| G | 1:0.1 | 1.04 | 1.27 | — | 2 | Very good |
| H | 1:0.1 | 1.82 | 1.99 | — | 5 | Good |
| I | 1:0.1 | 8.93 | 22.04 | — | 19 | Poor |
| J | 1:0.1 | 13.67 | 28.89 | — | 24 | Poor |
| K | 1:0.05 | 0.76 | 1.04 | — | 0.5 | Excellent |
| L | 1:0.05 | 0.94 | 1.55 | — | 0.5 | Excellent |
| M | 1:0.05 | 12.99 | 56.6 | — | 87 | Very poor |
| N | 1:0.05 | 26.75 | 47.3 | — | 89 | Very poor |
| O | 1:0.05 | 5.87 | 30.05 | — | 31 | Very poor |
| P | 1:0.05 | 1.52 | 2.51 | — | 0 | Excellent |
| Q | 1:0.05 | 0.88 | 2.15 | — | 0 | Excellent |
| R | 1:0.05 | 1.36 | 5.23 | — | 2 | Very good |
| S | 1:0.1 | — | — | — | — | Oily paste |
| T | 1:0.3 | — | 25 | 88 | 98 | Very poor |
| U | 1:0.5 | — | 0.52 | 0.65 | 0 | Excellent |
| V | 1:1 | — | 0.78 | 1.27 | 0 | Excellent |
| W | 1:2 | — | 0.55 | 0.68 | 0 | Excellent |
| X | 1:0.1 | — | — | — | — | Oily paste |
| Y | 1:0.2 | — | 40.3 | 131.12 | 98 | Very poor |
| Z | 1:0.4 | — | 1.02 | 16.96 | 95 | Very poor |
| α | 1:0.1 | — | — | — | — | Oily paste |
| β | 1:0.5 | — | 0.82 | 2.57 | 0 | Excellent |
| ψ | 1:1 | — | 0.53 | 0.72 | 0 | Excellent |
| δ | 1:2 | — | 0.72 | 1.17 | 0 | Excellent |
| ε | 1:0.5 | — | 0.46 | 0.66 | 0 | Excellent |
| φ | 1:1 | — | 0.66 | 0.98 | 0 | Excellent |
| γ | 1:2 | — | 0.58 | 0.78 | 0 | Excellent |
| η | 1:0.5 | — | 0.46 | 0.66 | 0 | Excellent |
| ι | 1:1 | — | 0.52 | 0.72 | 0 | Excellent |
| control (only silica) | — | — | 0.67 | 0.92 | 0 | Excellent |

TABLE 3

Average capsule size and reconstitution rating following redispersion of the capsules in acidic media (pH = 2, adjusted with hydrochloric acid) after 2 months of storage (measured using Malvern Mastersizer)

| Row (from Table 1) | Oil: particle ratio | Average drop size (μm) | D (v, 0.9) (μm) | Vol % above 10 μm | Reconstitution mark |
|---|---|---|---|---|---|
| S | 1:0.1 | — | — | — | Oily paste |
| T | 1:0.3 | 54.6 | 133.6 | 98 | Very poor |
| U | 1:0.5 | 4.7 | 10.1 | Below 5 | Good |
| V | 1:1 | 2.39 | 7.42 | Below 2 | Very good |
| W | 1:2 | 0.55 | 0.68 | 0 | Excellent |
| X | 1:0.1 | — | — | — | Oily paste |
| Y | 1:0.2 | 105.2 | 167 | 98 | Very poor |
| Z | 1:0.4 | 3 | 39.3 | 50 | Very poor |
| α | 1:0.1 | — | — | — | Oily paste |
| control (only silica) | — | 0.64 | 0.93 | 0 | Excellent |

It is clear that the capsules of experiments U, V and W showed the best re-dispersibility and reconstitution after 2 months of storage (nb. after 8 months of storage, the respective average drop size of U, V and W, were 4.34 μm, 2.59 μm and 1.65 μm, against 3.34 μm of the control). These capsules were produced in the presence of a relatively low amount of electrolyte (i.e. $1 \times 10^{-4}$ M) and with an oil to nanoparticle mass ratio of at least 1:0.5. They were prepared from negatively charged oil droplets (stabilised with lecithin). It is considered that for such negatively charged oil droplets, an oil to nanoparticle ratio of at least 1:0.2 is required to achieve droplets that are wholly coated in nanoparticles.

On the other hand, for positively charged oil droplets (e.g. stabilised with oleylamine), it is considered that the droplets interact more strongly with the nanoparticles and, therefore, the minimum oil to nanoparticle ratio is less; in particular, an oil to nanoparticle mass ratio of at least 1:0.05 is believed to be required to produce dried capsules that can be re-dispersed to form a capsule-based emulsion which is substantially identical or similar to that from which the dried formulation was prepared. This ratio is believed to result in the production of wholly coated droplets, however, it is preferable to use an oil to nanoparticle mass ratio of at least 1:0.1.

The optimum ratio of nanoparticles (g/cm³) to lecithin (g/cm³) has been found to be 5:1 when nanoparticles congregate from the oil phase. The optimum ratio of nanoparticles (g/cm³) to oleylamine (g/cm³) has been found to be 1:10 when the nanoparticles congregate from either the oil or the water phase.

EXAMPLE 1 a) Preparation and Characterisation of Emulsion Stabilised by Lecithin

Lecithin (0.6 g) stabiliser was dissolved in triglyceride (Miglyol 812™) (10 g), and then added to water (total sample weight: 100 g) under mixing using a rotor-stator homogeniser (11,000 rpm, 10 minutes, pH=6.95±0.2). Alternatively, a high pressure homogeniser (5 cycles, 5 mBars) can be used for production of the emulsion. After 24 hours, the emulsion was characterised in terms of size (laser diffraction Malvern Mastersizer) and zeta potential (PALS). Droplet size distribution is shown in FIG. 9a and FIG. 9b. The droplet size ranges from 0.20-0.86 µm.

b) Preparation of Nanoparticles

Figure 8:
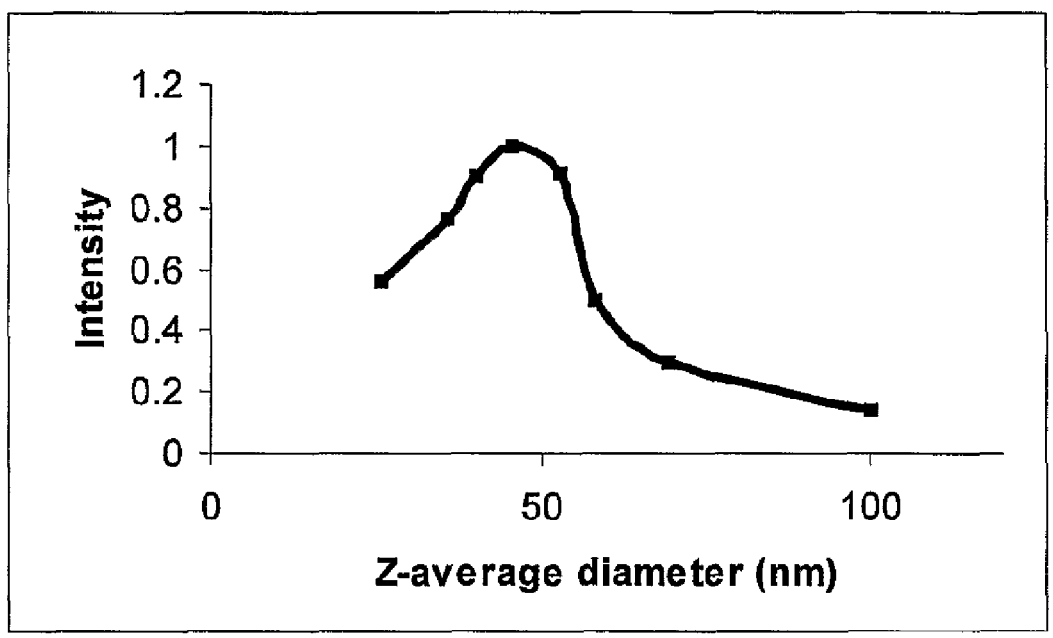

An aqueous dispersion of silica (Aerosil®) nanoparticles (1 wt %) was prepared by sonication over at least a one hour period. FIG. 8 shows that the average silica nanoparticle size was approximately 50 nm.

c) Capsule Formation

Emulsion formed in step (a) and nanoparticle dispersion (b) were mixed together. Subsequently, the volume of the mixture can be varied if desired by the addition of water. The salt concentration can be in the range of $1 \times 10^{-4}$ to $1 \times 10^{-1}$.

d) Drying—Removal of Continuous Phase

In order to prepare dry emulsion powders, an emulsion and hydrophilic silica dispersion were mixed in 20 ml vials and spray-dried under following conditions: flow rate 5 ml/min., aspirator setting 10, air flow 0.6 m$^3$/min, inlet temperature 160° C. and outlet temperature 85° C.

e) Redispersion and Characterisation of Capsules

Emulsions were redispersed in phosphate buffer (pH=7.2) and acidic media (pH=2) and the drop size distribution measured using a Malvern Mastersizer and Malvern Zetasizer Nano. Dry emulsion powders were imaged using SEM. Scanning electron microscopy was performed using a Philips SEM 515, operating at 15 kV. A thin layer of the samples was placed on double adhesive tape, sticked on SEM-stubs. The samples were coated with gold by a Balzers SCD 050, Balzer Union AG sputter prior to microscopy. The SEM images showed mono-disperse, smooth, spherical capsules which maintain their structural integrity even under the high vacuum required during imaging. There was no evidence of capsule aggregation as is often observed with SEM images of silica nanoparticles themselves. The capsules imaged had diameters within the range 100 to 300 nm indicating that the capsules are discrete oil droplets coated with at least one layer of nanoparticles.

EXAMPLE 2 a) Preparation of Emulsions

Simple Oil/Water lipid emulsions, containing 10% a 20% triglyceride (Miglyol® 812) as the oil phase, were prepared by high-pressure homogenizer at 500-1000 bar and ambient temperature. Negatively and positively charged emulsion oil droplets have been achieved by using lecithin and oleylamine respectively, as emulsifiers initially added to the oil phase. In the case of silica incorporated emulsions, silica nanoparticles were added to the oil phase or aqueous phase of emulsions, initially stabilised by lecithin or oleylamine, and sonicated for 60 minutes before homogenisation.

b) Size Analysis

Size measurements were carried out using laser diffraction by Malvern® Mastersizer (Malvern Instruments, UK) following appropriate dilution of samples with MiliQ water.

c) Freeze-Fracture Scanning Electron Microscopy

A freeze-fracture SEM technique (Philips XL 30 FEG scanning electron microscope with Oxford CT 1500 cryotransfer system) was used to image the oil droplets. The precise method for effective imaging of the droplets depends on the sample properties such as nanoparticle type and coverage. Generally, the methodology contains emulsion cryofixation, fracturing, etching, platinum coating and imaging.

d) Physical Stability Tests

Long-term physical stability of emulsions was assessed by size analysis of emulsion droplets at determined for intervals up to 3 months storage at ambient temperature.

D (v, 0.5), D (v, 0.9) and specific surface area were considered as indicators of physical stability of emulsions.

e) Visual Inspection

Organoleptic characteristics (i.e. evidence of creaming and coalescence) of emulsions have been recorded in parallel with size analysis. (nb. since oil is less dense than the water each oil drop is prone to floating upwards. This process is called creaming—the oil droplets will gradually form a dense layer at the top of the sample). The degree of creaming and phase separation is assessed by visual observation of emulsions at given time intervals. Coalescence can be determined by monitoring the mean droplet diameter of the emulsions during storage period. Organoleptically, the appearance of large oil droplets or a layer of free oil on the emulsion surface is the indicators of a coalesced emulsion.

EXAMPLE 3 a) Long-Term Physical Stability

Long term physical stability of emulsions has been improved in the presence of silica nanoparticles.

Figure 9:
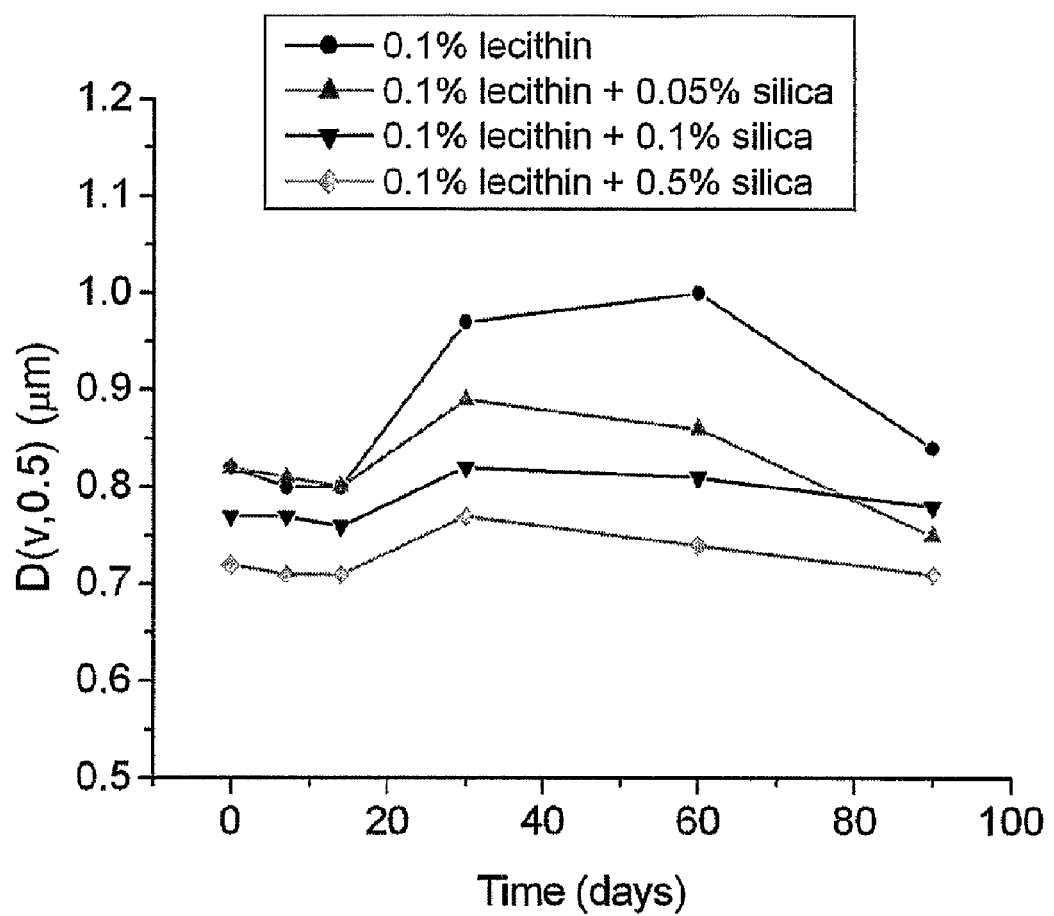

D (v, 0.9) of emulsions initially stabilised by lecithin, in the absence and presence of silica nanoparticles has been shown in (FIG. 9). D (v, 0.9) of silica-added emulsions was effectively unchanged during storage at room temperature for 3 months, whereas emulsions solely stabilised by lecithin have shown a 3-fold increase in D (v, 0.9).

EXAMPLE 4

In this example, dried capsule formulations were prepared from liposomes.

a) Liposome Preparation 0.3317 g lecithin and 0.1085 g cholesterol were dissolved in 20 ml chloroform and evaporated under vacuum. 20 ml MilliQ water was added with periodic sonication.

Liposomal dispersions were mixed with aqueous dispersions of silica nanoparticles and spray-dried using standard procedure.

Sample 1: Liposome dispersion 5 g and 95 g of 1 wt % silica nanoparticle dispersion;

Sample 2: Liposome dispersion 5 g and 95 g 5 wt % silica nanoparticle dispersion; and Sample 3: Liposome dispersion 30 g and 70 g 5 wt % silica nanoparticle dispersion.

b) Reconstitution in MilliQ Water After 24 Hours

The reconstitution of liposome-based capsules is shown in Table 4 below. The dried liposome capsules showed good re-dispersion properties, with the size distribution of the re-dispersed capsules being within the range of 0.5 to 5 µm.

TABLE 4

| Sample | z-average drop size (µm) | Polydispersibility index (PDI) | Zeta potentials (mV) |
| --- | --- | --- | --- |
| 1 | 5.1 | 0.305 | −4.94 ± 5.5 |
| 2 | 3.44 | 1.000 | −19.4 ± 16.4 |
| 3 | 2.43 | 0.2 | −26.1 ± 21.8 |

EXAMPLE 5 a) General Preparation Method:

Miglyol 10 g

Lecithin 0.6 g or Oleylamine 1 g

Silica 0.2-0.5 g

Polymer aqueous dispersion (hydroxypropyl methyl cellulose 1 wt % or chitosan 0.5 wt % or carbomer 0.1 wt %) to 100.0

Lecithin or oleylamine is dissolved in Miglyol and silica is added and redispersed in Miglyol. After polymer dispersion addition, the mixture is sonicated for 40 minutes and spray dried using standard procedures.

Samples were investigated for re-dispersibility in phosphate buffer, pH=7.2 using Malvern Zetasizer Nano after 24 hours storage at RT.

The re-dispersibility of samples is shown in Tables 5 to 10 (where PDI is the polydispersibility index):

i) Formulation 1:

Migliol 10 g

Oleylamine 1 g

Silica 0.2 g

Polymer aqueous dispersion (hydroxypropylmethyl cellulose 1 wt %) to 100.0

TABLE 5

| Before Spray Drying | | | dry powder re-dispersion in buffer | | |
|---|---|---|---|---|---|
| z-average drop size (μm) | PDI | Zeta potentials (mV) | z-average drop size | PDI | Zeta potentials (mV) |
| 0.364 | 0.375 | +35.4 ± 5.24 | 0.932 | 0.123 | +19.9 ± 7.03 | ii) Formulation 2:

Migliol 10 g

Oleylamine 1 g

Silica 0.5 g

Polymer aqueous dispersion (hydroxypropylmethyl cellulose 1 wt %) to 100.0.

TABLE 6

| Before Spray Drying | | | dry powder re-dispersion in buffer | | |
|---|---|---|---|---|---|
| z-average drop size (μm) | PDI | Zeta potentials (mV) | z-average drop size | PDI | Zeta potentials (mV) |
| 0.324 | 0.445 | +35.5 ± 8.54 | 1.05 | 0.123 | +18.8 ± 10.2 | iii) Formulation 3:

Migliol 10 g

Lecithin 0.6 g

Silica 0.5 g

Polymer aqueous dispersion (hydroxypropylmethyl cellulose 1 wt %) to 100.0.

TABLE 7

| Before Spray Drying | | | dry powder re-dispersion in buffer | | |
|---|---|---|---|---|---|
| z-average drop size (μm) | PDI | Zeta potentials (mV) | z-average drop size | PDI | Zeta potentials (mV) |
| 0.451 | 0.449 | −6.02 ± 18 | 2.16 | 0.385 | −10.1 ± 9.31 | iv) Formulation 4:

Migliol 10 g

Oleylamine 1 g

Silica 0.5 g

Polymer aqueous dispersion (carbomer 0.1 wt %) to 100.0.

TABLE 8

| Before Spray Drying | | | dry powder re-dispersion in buffer | | |
|---|---|---|---|---|---|
| z-average drop size (μm) | PDI | Zeta potentials (mV) | z-average drop size | PDI | Zeta potentials (mV) |
| 0.618 | 0.519 | −58.5 ± 10.1 | 1.9 | 0.907 | −29 ± 14.3 | v) Formulation 5:

Migliol 10 g

Lecithin 0.6 g

Silica 0.5 g

Polymer aqueous dispersion (carbomer 0.1 wt %) to 100.0.

TABLE 9

| Before Spray Drying | | | dry powder re-dispersion in buffer | | |
|---|---|---|---|---|---|
| z-average drop size (μm) | PDI | Zeta potentials (mV) | z-average drop size | PDI | Zeta potentials (mV) |
| 0.545 | 0.432 | −51.2 ± 5.13 | 2.8 | 1.000 | −25.8 ± 15.6 | vi) Formulation 6:

Migliol 10 g

Oleylamine 1 g

Silica 0.5 g

Polymer aqueous dispersion (chitosan 0.5 wt %) to 100.0.

TABLE 10

| Before Spray Drying | | | dry powder re-dispersion in buffer | | |
|---|---|---|---|---|---|
| z-average drop size (μm) | PDI | Zeta potentials (mV) | z-average drop size | PDI | Zeta potentials (mV) |
| 0.556 | 0.497 | +73.3 ± 12.5 | 1.53 | 0.450 | +48.5 ± 4.8 |

EXAMPLE 6

In this example, formulations of dried capsules were produced using oleylamine as an emulsion stabiliser and tested for re-dispersion and reconstitution after 24 hours and 3 months storage at room temperature.

a) Preparation and Characterisation of Emulsion Stabilised by Oleylamine

Oleylamine (1.0 g) stabiliser was dissolved in triglyceride (Miglyol 812™) (10 g), and then added to water (total sample weight: 100 g). Emulsion was produced using high pressure homogenizer (5 cycles, 5 mBars pressure). After 24 hours, the emulsion was characterised in terms of size (laser diffraction Malvern Mastersizer) and zeta potential (PALS). The droplet size ranges from 0.20-1.5 μm.

b) Preparation of Nanoparticles

An aqueous dispersion of silica (Aerosil®) nanoparticles (1 wt %) was prepared by sonication over at least a one hour period. FIG. 8 shows that the average silica nanoparticle size was approximately 50 nm.

c) Capsule Formation

Emulsion formed in step (a) and nanoparticle dispersion (b) were mixed together in the ratios shown in Table 11 below. Subsequently, the volume of the mixture can be varied if desired by the addition of water. The salt concentration can be in the range of $1 \times 10^{-4}$ to $1 \times 10^{-1}$.

d) Drying—Removal of Continuous Phase

In order to prepare dry emulsion powders, an emulsion and hydrophilic silica dispersion were mixed in 20 ml vials and spray-dried under following conditions: flow rate 5 ml/min., aspirator setting 10, air flow 0.6 m³/min, inlet temperature 160° C. and outlet temperature 85° C.

e) Redispersion and Characterisation of Capsules

Emulsions were redispersed in phosphate buffer (pH=7.2) and acidic media (pH=2) and the drop size distribution was measured using a Malvern Mastersizer and Malvern zetananosizer. Results are shown in Table 11.

TABLE 11

| Sample | Ratio of oil (wt):particles(wt) | Average drop size after 24 hours (μm) | Average drop size after 3 months (μm) |
|---|---|---|---|
| 1 | 1:0.1 | 3.65 | 2.5 |
| 2 | 1:0.3 | 11.5 | 6.17 |
| 3 | 1:0.5 | 12.66 | 5.25 |
| 4 | 1:1 | 6.84 | 3.31 |
| 5 | 1:2 | 6.37 | 6.7 |

Modifications and variations such as would be apparent to persons skilled in the art are deemed to be within the scope of the present invention. For example, although the invention is generally discussed with reference to emulsion droplets, the techniques discussed can generally be applied to liposomes, other vesicle systems and other similar vehicles. For example, at least one layer of nanoparticles may congregate at the phase interface of the lipid layer of a vesicle and the continuous phase in which the vesicle is dispersed.

The invention claimed is:

1. A method of producing a dried formulation for an active substance, said method comprising the steps of:
   (i) dispersing a lipidic medium into an aqueous phase so as to form a two-phase liquid system comprising an aqueous emulsion of droplets of said lipidic medium, each of said droplets having, at its surface, a phase interface, and wherein said lipidic medium comprises an active substance, and an emulsifier selected from lecithin and oleylamine;
   (ii) allowing silica nanoparticles provided to said two-phase liquid system to congregate at the phase interface to coat said surface of the droplets in at least one layer of said nanoparticles, wherein said at least one layer of nanoparticles provides sufficient structural integrity to the droplets to enable the subsequent removal of the aqueous phase, and wherein the average diameter of the nanoparticles is in the range of 5-80 nm, and the nanoparticles are provided at a mass ratio of the lipidic medium to nanoparticles of, when the emulsifier present is lecithin, at least 1:0.2 or, where the emulsifier present is oleylamine, at least 1:0.05; and
   (iii) removing the aqueous phase from the nanoparticle-coated droplets to produce a dried formulation.

2. The method of claim 1, wherein the nanoparticles have hydrophilic surfaces and the emulsifier is lecithin.

3. The method of claim 1, wherein the active substance is selected from nutriceutical substances, cosmetic substances and drug compounds.

4. The method of claim 1, wherein the active substance is selected from lipophilic drug compounds.

5. The method of claim 1, wherein the nanoparticles are provided by dispersing the nanoparticles in the lipidic medium prior to the formation of the two-phase liquid system in step (i).

6. The method of claim 1, wherein the nanoparticles are provided by dispersing the nanoparticles in both the lipidic medium and the aqueous phase prior to the formation of the two-phase liquid system in step (i).

7. The method of claim 1, wherein the nanoparticles have hydrophilic surfaces and the emulsifier is oleylamine.

8. The method of claim 1, wherein the droplets are coated with an inner and outer layer of nanoparticles, the nanoparticles of the inner layer having hydrophobic surfaces and the nanoparticles of the outer layer having hydrophilic surfaces.

9. The method of claim 1, wherein said nanoparticles have an average diameter of about 50 nm.

10. The method of claim 1, wherein the size of said nanoparticles is such that the ratio of nanoparticle size to the size of the nanoparticle-coated droplets is about 1:10.

11. The method of claim 1, wherein step (ii) is conducted in the presence of an amount of electrolyte in the range of $0.5 \times 10^{-4}$ to $1 \times 10^{-1}$ M.

12. The method of claim 11, wherein the electrolyte is NaCl.

13. The method of claim 12, wherein step (ii) is conducted in the presence of about $1 \times 10^{-4}$ NaCl.

14. The method of claim 1, wherein step (iii) is performed by spray drying.

15. The method of claim 1, wherein the nanoparticle-coated droplets of the dried formulation can be readily re-dispersed to form a two-phase liquid system which is substantially identical or similar in composition to that from which the dried formulation was prepared, after storage at room temperature for 24 hours.

* * * * *